US006372198B1

(12) United States Patent
Abbate

(10) Patent No.: US 6,372,198 B1
(45) Date of Patent: Apr. 16, 2002

(54) DENTIFRICE FOR THE MINERALIZATION AND REMINERALIZATION OF TEETH

(76) Inventor: Joseph M. Abbate, 24095 Farmington Rd., Farmington, MI (US) 48335

( * ) Notice: Subject to any disclaimer, the term of this patent is extended or adjusted under 35 U.S.C. 154(b) by 0 days.

(21) Appl. No.: 09/661,538

(22) Filed: Sep. 14, 2000

(51) Int. Cl.$^7$ .......................... A61K 7/16; A61K 31/12; A61K 7/28
(52) U.S. Cl. .................. 424/49; 514/690; 424/50
(58) Field of Search ................ 424/49–58; 514/690

(56) References Cited

U.S. PATENT DOCUMENTS

| | | | |
|---|---|---|---|
| 4,083,955 A | | 4/1978 | Grabenstetter et al. |
| 4,327,079 A | | 4/1982 | Aoki |
| 4,356,168 A | | 10/1982 | Harvey et al. |
| 4,357,317 A | | 11/1982 | Weyn et al. |
| 4,397,837 A | | 8/1983 | Raaf et al. |
| 4,425,324 A | | 1/1984 | Harvey et al. |
| 4,460,565 A | | 7/1984 | Weststrate et al. |
| 4,518,430 A | | 5/1985 | Brown et al. |
| 4,606,912 A | | 8/1986 | Rudy et al. |
| 4,654,373 A | * | 3/1987 | Bertelli .................. 514/690 |
| 5,378,461 A | * | 1/1995 | Neigut .................. 514/461 |
| 5,571,502 A | | 11/1996 | Winston et al. |
| 5,603,922 A | | 2/1997 | Winston et al. |
| 5,605,675 A | | 2/1997 | Usen et al. |
| 5,605,677 A | | 2/1997 | Schumann et al. |
| 5,614,175 A | | 3/1997 | Winston et al. |
| 5,618,549 A | | 4/1997 | Patat et al. |
| 5,645,853 A | | 7/1997 | Winston et al. |
| 5,817,296 A | | 10/1998 | Winston et al. |
| 5,833,954 A | | 11/1998 | Chow et al. |
| 5,833,957 A | | 11/1998 | Winston et al. |
| 5,853,704 A | | 12/1998 | Zhang |
| RE36,035 E | | 1/1999 | Usen et al. |
| 5,858,333 A | | 1/1999 | Winston et al. |
| 5,860,565 A | | 1/1999 | Winston et al. |
| 5,866,102 A | | 2/1999 | Winston et al. |
| 5,895,641 A | | 4/1999 | Usen et al. |
| 5,925,335 A | * | 7/1999 | Shuch et al. .................. 424/49 |
| 5,958,380 A | | 9/1999 | Winston et al. |
| 5,993,786 A | | 11/1999 | Chow et al. |
| 6,036,944 A | | 3/2000 | Winston et al. |
| 6,048,886 A | * | 4/2000 | Neigut .................. 514/712 |
| 6,200,550 B1 | * | 3/2001 | Masterson et al. ............ 424/49 |
| 6,207,137 B1 | * | 3/2001 | Shuch et al. .................. 424/49 |

FOREIGN PATENT DOCUMENTS

| | | | |
|---|---|---|---|
| JP | 54151933 A | * | 11/1979 |
| JP | 61286314 A | * | 12/1986 |
| SE | 9500610 A | * | 9/1995 |
| WO | 9415595 A | * | 7/1994 |
| WO | 9856336 A | * | 12/1998 |

OTHER PUBLICATIONS

"Oral Hygiene—Is It The Cue to Longevity?", *Journal of Longevity*, 2000 vol. 6/No. 3, pp 48–50.
Chlorella Products Ltd, Article: "NURTI–MIN Pro–Biotic Mineral Concentrate, The Ultimate Multi–Mineral Supplement" by John Claydon D. Hom, 1998.
American Chemical Society, Article: "Squeezing Out A Better Toothpaste", by Michael Prencipe, James G. Master, K. Penny Thomas & James Norfleet, Dec. 1995.
BC Cancer Agency, Article "Unconventional Cancer Therapies—Coenzyme Q/Ubiquinone", Feb. 2000.
National Cancer Institute, Article: "Coenzyme $Q_{10}$ (PDQ®)", Jun. 2000.
*The Journal of Clinical Dentistry*, vol. X, 1999, No. 1.

* cited by examiner

*Primary Examiner*—Shep K. Rose
(74) *Attorney, Agent, or Firm*—Harness, Dickey & Pierce, PLC

(57) ABSTRACT

Dentifrice compositions for mineralizing and remineralizing a surface or subsurface of at least one tooth, are described. The compositions primarily include at least one water soluble calcium salt, at least one water soluble phosphate salt, and at least one antioxidant, such as coenzyme Q10. Additionally, at least one water soluble non-toxic divalent metal compound, wherein the metal is other than calcium, such as magnesium, may also be added. Furthermore, at least one selenium-containing material, as well as at least one bromine-containing material, may also be added to the composition. The respective materials are then mixed and formed into a paste and applied to the tooth surface for a sufficient period of time to allow sufficient amounts of calcium and phosphate ions in the mixture to diffuse through the tooth surface, where the diffused ions react together to form an insoluble precipitate on the surface or subsurface of the tooth. The co-enzyme Q10, selenium, and bromine are believed to contribute to the overall health of the oval cavity, especially gum tissues.

14 Claims, No Drawings

DENTIFRICE FOR THE MINERALIZATION AND REMINERALIZATION OF TEETH

BACKGROUND OF THE INVENTION

1. Technical Field

The present invention relates generally to dentifrices, and more particularly to dentifrice compositions containing enhanced levels of minerals for mineralizing and remineralizing teeth, as well as various chemical compounds for promoting beneficial oral cavity health.

2. Discussion

A dentifrice is a substance or preparation used with a toothbrush to aid mechanical cleaning of the accessible surfaces of the teeth. A typical formulation for a dentifrice (e.g., toothpaste) contains varying amounts of humectants (e.g., glycerine, sorbital, propylene glycol, xylitol, polyethylene glycol), water, buffers/salts/tartar controls (e.g., tetrasodium pyrophosphate, sodium tripolyphosphate), organic thickeners and gums (e.g., sodium carboxylmethyl cellulose, cellulose ethers, xanthan gum, carrageenans, sodium alginate, and carbopols), inorganic thickeners (e.g., silica thickeners, sodium aluminum silicates, and clays), abrasives (e.g., hydrated silica, dicalcium phosphate digydrate, calcium carbonate, sodium bicarbonate, calcium pyrophosphate, and alumina), active ingredients (e.g., fluoride, and TRICLOSAN™), surfactants (e.g., sodium lauryl sulfate, sodium N-lauryl sarcosinate, pluronics, sodium lauryl sulfoacetate), and flavors and sweeteners (e.g., wintergreen, cinnamon, peppermint, etc.).

On the basis of clinical studies involving the use of dentifrices containing sodium monofluorophosphate, $Na_2PFO_3$, as the active ingredient have been accepted by the Council on Dental Therapeutics of the American Dental Association (ADA) as effective in helping to prevent caries. Examples of dentifrices containing sodium monofluorophosphate are Colgate with MFP and Macleans Fluoride. When incorporated in dentifrice formulations at a level of ca. 0.76%, sodium monofluorophosphate has been shown to be of benefit in 17–38% reduction of dental caries. These findings are in the same general range as those reported for dentifrices already accepted by the ADA that contain 0.4% stannous fluoride ($SnF_2$) (e.g., Crest and Aim).

In addition to the prevention of caries, there has been increasing interest by the dental health industry in the mineralization and remineralization of tooth enamel. Enamel is the term given to the bony outer surface of teeth. Enamel, as well as other structures of the tooth (e.g., dentin), are generally comprised of apatite (e.g., calcium phosphate in the form of calcium hydroxyapatite). Through malnutrition, disease, neglect, and certain dental procedures (e.g., bleaching), the tooth enamel can become demineralized and, as a result, subject to decay, thus leading to the formation of caries, lesions or cavities. For example, the consumption of sugary foods and beverages tends to enable the proliferation of plaque bacteria which in turn produces an acidic environment in the mouth which eventually leads to the demineralization of the tooth, absent appropriate intervention. The mode of demineralization is thought to involve the highly increased solubility of calcium phosphate salts in acidic oral cavity environments, as opposed to the high insolubility of calcium phosphate salts in normal pH oral cavity environments.

Although saliva, which is supersaturated with calcium and phosphate ions, aids somewhat in the natural remineralization process of enamel and dentin, it is a very slow process (due, in part, to the low solubility of calcium phosphate at the pH of saliva) whose benefits can be overcome in persistently acidic oral cavity environments. It is generally known that fluoride ions can enhance the natural remineralization process, thus, this is the reason why many commercially available dentifrices now contain various forms of fluoride ions, e.g., in the form of stannous fluoride or sodium monofluorophosphate.

One readily commercially available product that supposedly addresses the issue of mineralization and remineralization of various surface and subsurface tooth structures, such as enamel and dentin, is marketed under the tradename ENAMELON™ and is manufactured by Enamelon, Inc. (Cranbury, N.J.). With respect to ENAMELON™ brand dentifrice, the manufacturer claims that it contains a source of calcium ions, a source of phosphate ions, and a source of fluoride ions that act in manner that promotes the mineralization/remineralization of various surface and subsurface tooth structures, such as the enamel and the dentin.

A more complete discussion of tooth mineralization and remineralization can be found in the following U.S. patents, the entire specifications of which are incorporated herein by reference:

U.S. Pat. No. 4,083,955 discloses that two compositions containing respectively a cation and an anion, such as calcium ion and phosphate ion, are sequentially applied to dental enamel resulting in remineralization of subsurface dental enamel.

U.S. Pat. No. 4,327,079 discloses a dentifrice composition containing synthetic hydroxyapatite powder which is neutral or weakly alkaline or contains 0.1 to 20% by weight of NaCl and/or KCl and 0.003 to 3% by weight of $MgCl_2$.

U.S. Pat. No. 4,356,168 discloses an opacified dental cream which effects dental remineralization and reduces caries formation.

U.S. Pat. No. 4,357,317 discloses a dental cream composition containing a binary fluorine providing system which provides about 1000–1670 ppm (0.1–0.16% by weight) fluorine from sodium monofluorophosphate and sodium fluoride wherein sodium fluoride provides about 30–35% by weight of the fluorine in amount of about 300–580 ppm (0.02–0.058% by weight).

U.S. Pat. No. 4,397,837 discloses compositions for the remineralization and prevention of demineralization of the teeth of animals including humans in the form of two phases, one phase containing a water-soluble calcium compound and the other phase containing a water-soluble phosphate and optionally a water-soluble fluorine compound.

U.S. Pat. No. 4,425,324 discloses a hazed toothpaste which can effect dental remineralization and reduce caries formation.

U.S. Pat. No. 4,460,565 discloses a dentifrice containing two or more fluorine compounds, at least one soluble salt producing phosphate ions, and at least one substance providing calcium ions, and as a result thereof having good remineralization properties.

U.S. Pat. No. 4,518,430 discloses compositions that are remineralizers and dental cements, as well as methods for their use.

U.S. Pat. No. 4,606,912 discloses solutions for optimizing the environmental conditions within the human oral cavity which enhances the functioning of cells of the oral cavity and promotes remineralization of teeth.

U.S. Pat. No. 5,571,502 discloses non-aqueous compositions and methods utilizing same which are useful to remineralize subsurface dental enamel.

U.S. Pat. No. 5,603,922 discloses remineralization, without demineralization, by applying to the teeth a composition which is present in either one or in two phases and which does not react to any large extent until introduced into the oral cavity and upon such introduction does not rapidly precipitate.

U.S. Pat. No. 5,605,675 discloses the remineralization of dental enamel by applying to the teeth a composition which is present in two phases which do not react with one another until introduced into the oral cavity.

U.S. Pat. No. 5,605,677 discloses a toothpaste containing typical components and a combination of silicas and dicalcium phosphate dihydrate (brushite) as its polishing component provides for particularly good restoration of the surface of teeth.

U.S. Pat. No. 5,614,175 discloses non-aqueous compositions and methods utilizing same which are useful to remineralize subsurface dental enamel.

U.S. Pat. No. 5,618,549 discloses a method of treating a living organism having a disease associated with demineralization or mineralization defects of an existing bone by applying in a spongy portion of the bone or in a medullary canal of the bone at least one biocompatible and bioabsorbable calcium salt in the form of particles having dimensions less than 8 mm.

U.S. Pat. No. 5,645,853 discloses chewing gum compositions and methods utilizing same which are useful to remineralize surface dental enamel.

U.S. Pat. No. 5,817,296 discloses remineralization, without demineralization, by applying to the teeth a composition which is present in either one or in two phases and which does not react to any large extent until introduced into the oral cavity and upon such introduction does not rapidly precipitate.

U.S. Pat. No. 5,833,954 discloses anticarious delivery vehicles, specifically chewing gums, candies, confectioneries, toothpastes, dentifrices and gels.

U.S. Pat. No. 5,833,957 discloses remineralization, without demineralization, by applying to the teeth a composition which is present in either one or in two phases and which does not react to any large extent until introduced into the oral cavity and upon such introduction does not rapidly precipitate.

U.S. Pat. No. 5,853,704 discloses a multicomponent anticaries dentifrice composition and method of use therefore, having a first dentifrice component containing a fluoride ion source and a second dentifrice component containing a casein glycomacropeptide compound, wherein the components are physically separated before use and are combined immediately prior to application to the teeth, the dentifrice exhibiting enhanced enamel remineralization.

U.S. Pat. No. 5,858,333 discloses a two-part oral product capable of remineralizing subsurface lesions and/or mineralizing exposed dentinal tubules in teeth is composed of cationic and anionic discrete parts.

U.S. Pat. No. 5,895,641 discloses remineralization, without demineralization, of dental enamel by applying to the teeth a composition which is present in two phases which do not react with one another until introduced into the oral cavity.

U.S. Pat. No. 5,958,380 discloses a stable, single-part chewing gum product and methods of using same to effect remineralization of subsurface lesions in teeth and/or mineralization of exposed dentinal tubules.

U.S. Pat. No. 5,993,786 discloses anticarious delivery vehicles, specifically chewing gums, candies, confectioneries, toothpastes, dentifrices and gels.

U.S. Pat. No. 6,036,944 discloses a method for remineralizing one or more subsurface lesions in a tooth and/or mineralizing one or more exposed dentinal tubules in the tooth involves dispensing effective amounts of at least one water-soluble calcium salt, at least one water-soluble non-toxic divalent metal compound wherein the divalent metal is other than calcium, at least one water-soluble phosphate salt and, optionally, a water-soluble fluoride salt; mixing the salts and compound to form a non-carbonated mixture having a pH in water such that a non-carbonated aqueous solution containing the mixture has a pH of from 4.5 to about 7.0; and then applying the non-carbonated mixture as the non-carbonated aqueous solution to a surface of the tooth for a sufficient period of time to allow sufficient amounts of calcium, phosphate and, if present, fluoride, ions in the solution to diffuse into the subsurface of the tooth where the diffused ions then react to form an insoluble precipitate onto the lesions and/or exposed tubules, thereby remineralizing the lesions and/or mineralizing the tubules.

Although various dentifrice products that are currently available on the market appear to address the need for mineralization and remineralization of teeth, they do not address the need to provide for proper oral cavity health, including the protection of gum tissues from various diseases. The prevalence of various diseases that adversely affect gum tissues, such as gingivitis and periodontal disease, has lead to severe health consequences for many individuals, including the loss of their teeth and other related health problems. Although the aforementioned mineralization and remineralization of teeth aids somewhat in the overall health of the oral cavity, the need for proper care of the surrounding tissues, most notably the gums, must not be overlooked.

Therefore, there exists a need for dentifrice compositions containing enhanced levels of minerals for mineralizing and remineralizing teeth, as well as various chemical compounds for promoting beneficial oral cavity health.

SUMMARY OF THE INVENTION

Accordingly, it is an object of the present invention to provide a new and improved dentifrice composition.

It is another object of the present invention to provide a new and improved dentifrice composition that has enhanced levels of minerals for mineralizing and remineralizing teeth.

It is still another object of the present invention to provide new and improved dentifrice compositions containing enhanced levels of minerals for mineralizing and remineralizing teeth, as well as various chemical compounds for promoting beneficial oral cavity health.

In accordance with one embodiment of the present invention, a dentifrice composition is provided for mineralizing and remineralizing a surface or subsurface of at least one tooth, comprising:

at least one water soluble calcium salt;

at least one water soluble phosphate salt; and at least one antioxidant.

In accordance with another embodiment of the present invention, a dentifrice composition is provided for mineralizing and remineralizing a surface or subsurface of at least one tooth, comprising:

at least one water soluble calcium salt;

at least one water soluble phosphate salt;

at least one antioxidant; and at least one selenium-containing material.

In accordance with yet another embodiment of the present invention, a dentifrice composition is provided for mineralizing and remineralizing a surface or subsurface of at least one tooth, comprising:

at least one water soluble calcium salt;

at least one water soluble phosphate salt;

at least one antioxidant;

at least one selenium-containing material; and at least one bromine-containing material.

In accordance with still another embodiment of the present invention, a method is provided for mineralizing and remineralizing a surface or subsurface of at least one tooth, comprising:

providing at least one water soluble calcium salt;

providing at least one water soluble phosphate salt;

providing at least one antioxidant;

mixing said salts and antioxidant to form a mixture; and applying said mixture to the tooth surface for a sufficient period of time to allow sufficient amounts of calcium and phosphate ions in the mixture to diffuse through the tooth surface, where the diffused ions react together to form an insoluble precipitate on the surface or subsurface of the tooth.

In accordance with still yet another embodiment of the present invention, a method is provided for mineralizing and remineralizing a surface or subsurface of at least one tooth, comprising:

providing at least one water soluble calcium salt;

providing at least one water soluble phosphate salt;

providing at least one antioxidant;

providing at least one selenium-containing material;

mixing said salts, antioxidant, and material to form a mixture; and applying said mixture to the tooth surface for a sufficient period of time to allow sufficient amounts of calcium and phosphate ions in the mixture to diffuse through the tooth surface, where the diffused ions react together to form an insoluble precipitate on the surface or subsurface of the tooth.

In accordance with a further embodiment of the present invention, a method is provided for mineralizing and remineralizing a surface or subsurface of at least one tooth, comprising:

providing at least one water soluble calcium salt;

providing at least one water soluble phosphate salt;

providing at least one antioxidant;

providing at least one selenium-containing material;

providing at least one bromine-containing material;

mixing said salts, antioxidant, and materials to form a mixture; and applying said mixture to the tooth surface for a sufficient period of time to allow sufficient amounts of calcium and phosphate ions in the mixture to diffuse through the tooth surface, where the diffused ions react together to form an insoluble precipitate on the surface or subsurface of the tooth.

A more complete appreciation of the present invention and its scope can be obtained from understanding the following detailed description of the invention and the appended claims.

DETAILED DESCRIPTION OF THE INVENTION

The present invention is primarily directed to dentifrice compositions, and particularly those dentifrice compositions containing enhanced levels of minerals for mineralizing and remineralizing teeth, as well as various chemical compounds for promoting beneficial oral cavity health.

In accordance with one aspect of the present invention, not only are enhanced levels of water soluble calcium salts and phosphate salts employed, but divalent metals, such as magnesium, strontium, tin, and zinc, are optionally employed as well. These divalent metals aid in the aforementioned mineralization and remineralization processes.

Water-soluble calcium salts and compounds suitable for practicing the present invention are, by way of a non-limiting example, calcium chloride, calcium bromide, calcium nitrate, calcium acetate, calcium gluconate, calcium benzoate, calcium glycerophosphate, calcium formate, calcium fumarate, calcium lactate, calcium butyrate and calcium isobutyrate, calcium malate, calcium maleate, calcium propionate, or mixtures of water-soluble calcium compounds. In the compositions of the invention for the mineralization/remineralization of human dental enamel, the calicum ions are preferably present in a range from about at least 18 mmol/L to about 1.5 mol/L.

Water-soluble inorganic phosphate salts and compounds suitable for practicing to the present invention are, by way of a non-limiting example, alkali salts and ammonium salts of orthophosphoric acid, such as potassium, sodium or ammonium orthophosphate, monopotassium phosphate, dipotassium phosphate, tripotassium phosphate, monosodium phosphate, disodium phosphate and trisodium phosphate. The concentration of the phosphate ions is preferably about at least 18 mmol/L to about 1.5 mol/L.

If desired, water-soluble salts yielding both calcium and phosphate ions, such as monobasic-calcium orthophosphate, may be employed.

With respect to the stabilizing divalent metal compound, it is also possible to employ any water-soluble, non-toxic divalent metal compound which will stabilize the calcium and phosphate ions so that they do not rapidly or prematurely precipitate before diffusing into the teeth. In practice, however, it has been found that at least one member selected from the group consisting of magnesium, strontium, tin, and zinc, with magnesium being preferred, are the most effective in stabilizing the system.

Suitable magnesium compounds are, by way of a non-limiting example, magnesium acetate, magnesium ammonium sulfate, magnesium benzoate, magnesium bromide, magnesium borate, magnesium citrate, magnesium chloride, magnesium gluconate, magnesium glycerophosphate, magnesium hydroxide, magnesium iodide, magnesium oxide, magnesium propionate, magnesium D-lactate, magnesium DL-lactate, magnesium orthophosphate, magnesium phenolsulfonate, magnesium pyrophosphate, magnesium sulfate, magnesium nitrate, and magnesium tartrate.

Suitable strontium compounds are, by way of a non-limiting example, strontium acetate, strontium ammonium sulfate, strontium benzoate, strontium bromide, strontium borate, strontium caprylate, strontium carbonate, strontium citrate, strontium chloride, strontium gluconate, strontium glycerophosphate, strontium hydroxide, strontium iodide, strontium oxide, strontium propionate, strontium D-lactate, strontium DL-lactate, strontium pyrophosphate, strontium sulfate, strontium nitrate, and strontium tartrate.

Suitable tin compounds are, by way of a non-limiting example, stannous acetate, stannous ammonium sulfate, stannous benzoate, stannous bromide, stannous borate, stannous carbonate, stannous citrate, stannous chloride, stannous gluconate, stannous glycerophosphate, stannous hydroxide, stannous iodide, stannous oxide, stannous propionate, stannous D-lactate, stannous DL-lactate, stannous orthophosphate, stannous pyrophosphate, stannous sulfate, stannous nitrate, and stannous tartrate.

Suitable zinc compounds are, by way of a non-limiting example, zinc acetate, zinc ammonium sulfate, zinc benzoate, zinc bromide, zinc borate, zinc citrate, zinc chloride, zinc gluconate, zinc glycerophosphate, zinc hydroxide, zinc iodide, zinc oxide, zinc propionate, zinc D-lactate, zinc DL-lactate, zinc pyrophosphate, zinc sulfate, zinc nitrate, and zinc tartrate. Preferred zinc compounds are zinc acetate, zinc chloride, zinc sulfate, and zinc nitrate.

The compositions of the present invention for the remineralization or prevention of demineralization of human teeth may also contain water-soluble fluoride compounds, the caries-prophylactic activity of which has for a long time been considered to be established. When two phase systems are employed, these compounds are preferably present in the phase containing phosphate in order to avoid the formation of sparingly soluble calcium fluoride.

Suitable fluoride compounds are the alkali fluorides such as, by way of a non-limiting example, sodium, potassium, lithium or ammonium fluoride, tin fluoride, indium fluoride, zirconium fluoride, copper fluoride, nickel fluoride, palladium fluoride, fluorozirconates such as sodium, potassium or ammonium fluorozirconate or tin fluorozirconate, fluorosilicates, fluoroborates, fluorostannites.

Organic fluorides, such as the known amine fluorides are also suitable for use in the compositions of the invention.

Water-soluble alkali metal monofluorophosphates such as sodium monofluorophosphate, lithium monofluorophosphate and potassium monofluorophosphate, preferably, sodium monofluorophosphate may be employed. In addition, other water-soluble monofluorophosphate salts may be employed including, by way of a non-limiting example, ammonium monofluorophosphate aluminum monofluorophosphate, and the like. If monofluorophosphate salts are used as the fluoride source in two-component systems, they could be present in the first component along with the calcium cations without departing from the present invention. However, this is less desirable due to the potential loss of fluoride.

Suitable toothpastes and gels can be made by employing, in addition to the mineralizing/remineralizing agents of the invention, from about 0.5% to 65%, preferably from about 5% to 40%, of an abrasive, from about 0.2% to 5% of a sudsing agent, from about 0.1% to 5% of a binding agent, from 0% to 50% of a humectant, and the balance, water and other minor ingredients. From about 1.0% to 10.0% of an inorganic thickener such as hydrated silica may be added.

In the case of two separate components, the pH of a component of such toothpaste or gel comprised of the active cationic or anionic ingredients each has a pH of more than about 3. The mixture of the two portions which is placed in the mouth, however, must have a pH of from 4.5 to about 7.0, preferably from about 5.0 to about 7.0, more preferably from about 5.0 to about 5.75. The pHs of the cationic portion and the anionic portion can be adjusted so long as the above pH parameters are not exceeded.

Suitable abrasives include silica xerogels. Other conventional toothpaste abrasives can be used in the compositions of this invention, and include beta phase calcium pyrophosphate, dicalcium phosphate dihydrate, anhydrous calcium phosphate, calcium carbonate, zirconium silicate, and thermosetting polymerized resins. Silica aerogels and the insoluble metaphosphates such as insoluble sodium metaphosphate can be used. Mixtures of abrasives can also be used.

Suitable sudsing agents are those which are reasonably stable and form suds throughout the period of application. Preferably, non-soap anionic or nonionic organic synthetic detergents are employed. Non-limiting examples of such agents are water-soluble salts of alkyl sulfate having from 10 to 18 carbon atoms in the alkyl radical, such as sodium lauryl sulfate, water-soluble salts of sulfonated monoglycerides of fatty acids having from 10 to 18 carbon atoms, such as sodium monoglyceride sulfonate, salts of $C_{10}$–$C_{18}$ fatty acid amides of taurine, such as sodium N-methyl taurate, salts of $C_{10}$–$C_{18}$ fatty acid esters of isethionic acid, and substantially saturated aliphatic acyl amides of saturated monoaminocarboxylic acids having 2 to 6 carbon atoms, and in which the acyl radical contains 12 to 16 carbon atoms, such as sodium-N-lauryl sarcoside. Mixtures of two or more sudsing agents can be used.

A binding material is added to thicken and provide a desirable consistency for the present compositions. Suitable thickening agents are, without limitation, water-soluble salts of cellulose ethers, such as sodium carboxymethyl cellulose, hydroxypropyl cellulose, and hydroxyethyl cellulose. Natural gums such as gum karaya, gum arabic, carrageenan and gum tragacanth, can also be used. Colloidal magnesium aluminum silicate, silica aerogels, silica xerogels, fumed silica, or other finely divided silica can be used as part of the thickening agent for further improved texture. A preferred thickening agent is xanthan gum.

It is also desirable to include some humectant material in a toothpaste or gel to keep it from hardening. Suitable humectants include glycerine, sorbitol, polyethylene glycol, propylene glycol, and other edible polyhydric alcohols as well as mixtures thereof.

Toothpaste or gel compositions may also contain flavoring agents such as oil of wintergreen, oil of peppermint, oil of spearmint, oil of sassafras, and oil of clove, as well as cinnamon.

Toothpaste or gel compositions may further contain sweetening agents such as saccharin, dextrose, luvulose, sodium cyclamate, and aspartame. Mixtures of sugar with a sweetener, e.g., sucralose, are also envisioned.

In accordance with another aspect of the present invention, trace minerals, such as selenium and bromine, that are believed to have beneficial effects on the overall health of the oral cavity are also preferably employed in the dentifrice composition of the present invention. Although these trace minerals may be added to the dentifrice composition of the present invention from various chemical suppliers, it is preferred to use mineral water from a natural source, such as a spring. Examples of such naturally-occurring springs are located in the southeastern portion of Michigan, for example in the Mount Clemens area, and have been identified as having some of the highest, if not the highest, levels of naturally-occurring minerals, as well as trace minerals, of any springs in the world. Although the exact mechanisms of the health benefits have not been thoroughly explained, it is generally recognized that several different types of trace minerals, such as selenium and bromine, have been identified as having potentially beneficial effects on overall health, and specifically on the health of the oral cavity, either acting alone or in concert with other minerals, vitamins, and/or enzymes.

By way of a non-limiting example, a suitable mineral water composition (taken from a spring in Mount Clemens, Mich.) in accordance with one aspect of the

EXAMPLE I

| INGREDIENT | AMOUNT (grains/gallon) |
|---|---|
| Ferrous carbonate | <0.13 |
| Ferrous sulfide | <0.16 |
| Lithium chloride | 9.3 |
| Magnesium carbonate | <0.085 |
| Magnesium bromide | 1600 |
| Magnesium chloride | 850 |
| Magnesium iodide | 0.77 |
| Magnesium sulfate | 70 |
| Potassium chloride | 160 |
| Potassium sulfate | 102 |
| Rubidium | 0.26 |
| Sodium carbonate | <0.11 |
| Sodium diborate | 12.5 |
| Sodium chloride | 4500 |
| Sodium selenite | <0.013 |
| Sodium silicate | 0.28 |
| Sodium sulfite | 0.37 |
| Sodium sulfate | 83 |
| Sodium tellurite | <0.11 |
| Strontium sulfate | 28 |
| Sulfur | 80 | present invention is presented below:

As can be noted, the level of the various minerals and trace minerals in the sample of spring water is relatively much higher than those levels found in ordinary tap water or even bottled spring water.

Accordingly, in accordance with a preferred embodiment of the present invention, the dentifrice composition of the present invention preferably contains at least one selenium-containing material and/or at least one bromine-containing material. These materials are preferably non-toxic, either in organic or inorganic form, or elemental, compound, and/or chelated form.

In accordance with another aspect of the present invention, chemical compounds, including antioxidants such as selenium and coenzyme Q10, are also employed that are believed to have beneficial effects on the overall health of the oral cavity.

Coenzyme Q10 (also known as Co Q10, Q10, vitamin Q10, ubiquinone, or ubidecarenone) is a benzoquinone compound synthesized naturally in the human body. The "Q" and the "10" in the name refer to the quinone chemical group and the 10 isoprenyl chemical subunits, respectively, that are part of this compound's structure. The term "coenzyme" denotes it as an organic (contains carbon atoms), nonprotein molecule necessary for the proper functioning of its protein partner (an enzyme or enzyme complex). Coenzyme Q10 is used by the cells of the body in a process known variously as aerobic respiration, aerobic metabolism, oxidative metabolism, or cell respiration. Through this process, energy for cell growth and maintenance is created inside cells in compartments called mitochondria. Coenzyme Q10 is also used by the body as an endogenous antioxidant. An antioxidant is a substance that protects cells from free radicals, which are highly reactive chemicals, often containing oxygen atoms, capable of damaging important cellular molecules such as DNA and lipids.

It has recently been suggested that oral and/or intravenous administration of coenzyme Q10 may be beneficial in the treatment of various diseases, including periodontal disease. In certain clinical studies, it has been observed that the oral administration, for example, in the form of pills, capsules, and powders, of coenzyme Q10 has alleviated the symptoms of periodontal disease, including inflammation, swelling, and bleeding of the gum tissues.

Accordingly, in accordance with a preferred embodiment of the present invention, the dentifrice composition of the present invention preferably contains an amount of coenzyme Q10. It is believed that the coenzyme Q10, when present in sufficient amounts, will have a therapeutic effect on the soft tissues surrounding, adjacent to, or in proximity to, the tooth structure (e.g., gum tissues) and thus aid in the prevention and treatment of various periodontal diseases. The form of the coenzyme Q10, for example, powder or liquid, is not thought to be critical.

By way of a non-limiting example, a dentifrice composition, in accordance with one aspect of the present invention, is presented below:

EXAMPLE II

| INGREDIENT | AMOUNT (WEIGHT PERCENTAGE) |
|---|---|
| Deionized water | 130 ml (16.26) |
| Mineral water | 40 ml (5.0) |
| Sodium saccharin | 0.7 g (0.086) |
| Methylparaben | 1.3 g (0.16) |
| Sodium carboxymethylcellulose (CMC) | 2.2 g (0.28) |
| Sorbitol (70 vol. %) | 200 ml (25.0) |
| Glycerine (97 vol. %) | 45 ml (5.625) |
| Dicalcium phosphate dihydrate | 330 g (41.25) |
| Dicalcium phosphate anhydrous | 25 g (3.125) |
| Carageenan (marine colloids) | 10 g (1.25) |
| Sodium monofluorophosphate (optional) | 0.79 g (0.1) |
| Coenzyme Q10 (optional) | 2.4 g (0.31) |
| Sodium lauryl sulfate | 13 g (1.625) |
| Sodium sulfoacetate (optional) | 23 g (2.87) |
| Wintergreen flavoring | 0.6 ml (0.075) |
| Cinnamon flavoring | 4 ml (0.5) |

As previously noted, the dentifrice composition of the present invention is then formed into a suitable paste, gel, powder, or liquid, for use by a consumer. The consumer then places an appropriate amount (e.g., 2.0–2.5 g of the dentifrice per application, preferably three applications per day) of the dentifrice composition of the present invention on a toothbrush and proceeds to brush in a normal manner, whereupon the key ingredients of the dentifrice composition of the present invention, i.e., the calcium ions and phosphate ions, aided by the optional magnesium, contact the teeth and act in manner to cause the mineralization and remineralization of various surfaces and subsurfaces of the teeth, as previously described. The other optional ingredients of the dentifrice composition of the present invention, i.e., the various trace minerals such as selenium and bromine, as well as the coenzyme Q10, act to aid in the overall health of the oral cavity, especially the gum tissues. If the level of the coenzyme Q10 needs to be raised in order to have a therapeutic effect, additional amounts of coenzyme Q10 may be added to the dentifrice composition of the present invention. Additionally, because coenzyme Q10 may have a tendency to cause the dentifrice composition to take on a slightly orange color, whitening agents, such as titanium dioxide, may be employed to restore a whiter appearance to the dentifrice composition.

The foregoing description is considered illustrative only of the principles of the invention. Furthermore, because numerous modifications and changes will readily occur to those skilled in the art, it is not desired to limit the invention to the exact construction and process shown as described above. Accordingly, all suitable modifications and equivalents that may be resorted to that fall within the scope of the invention as defined by the claims that follow.

What is claimed is:

1. A dentifrice composition for mineralizing and remineralizing a surface or subsurface of at least one tooth, comprising:
   at least one water soluble calcium salt;
   at least one water soluble phosphate salt;
   about 0.1 to about 0.4 weight percent ubiquinone; and
   mineral water.

2. The invention according to claim 1, wherein the ubiquinone has a therapeutic effect on a soft tissue in proximity to the at least one tooth.

3. The invention according to claim 1, further comprising at least one water soluble non-toxic divalent metal compound wherein the metal is other than calcium.

4. The invention according to claim 3, wherein the divalent metal is selected from the group consisting of magnesium, strontium, tin, zinc, and combinations thereof.

5. The invention according to claim 1, further comprising at least one selenium-containing material.

6. The invention according to claim 1, further comprising at least one bromine-containing material.

7. The invention according to claim 1, wherein the composition is in the form of a paste.

8. The invention according to claim 1, further comprising at least one water soluble fluoride salt.

9. The dentifrice of claim 1, further comprising:
   a mineral water;
   a thickener;
   a humectant;
   an abrasive;
   a foaming agent;
   a flavor ingredient; and
   mixtures thereof.

10. The dentifrice of claim 9, said mineral water comprises: selenium; strontium; lithium; carbonate; sodium chloride; and sulfur.

11. A dentifrice for a tooth and an oral cavity comprising de-ionized water, a thickener, a humectant, and abrasive, a foaming agent, and mixtures thereof:
    adding a mineral water in the amount of about 7 to about 8 weight percent of the dentifrice; and
    adding a ubiquinone in the amount of about 0.1 to about 0.4 weight percent of the dentifrice.

12. The dentifrice of claim 11, wherein the mineral water comprises: selenium; strontium; lithium; carbonate; sodium chloride; and sulfur.

13. A dentifrice for a tooth and an oral cavity comprising:
    de-ionized water;
    a thickener;
    a humectant;
    an abrasive;
    a foaming agent;
    a water soluble calcium salt;
    a water soluble phosphate salt;
    about 0.1 to about 0.4 weight percent ubiquinone;
    a carbonate salt selected from a group consisting of Ferrous carbonate, Magnesium carbonate, and Sodium carbonate;
    a sulfide salt comprising Ferrous sulfide;
    a lithium salt comprising Lithium chloride;
    a magnesium salt selected from a group consisting of Magnesium bromide and Magnesium chloride;
    an iodide salt comprising magnesium iodide;
    a sulfate salt selected from a group consisting of Magnesium sulfate, Potassium sulfate, and Sodium sulfate;
    a potassium salt comprising Potassium chloride;
    rubidium;
    a boron salt comprising Sodium biborate;
    a sodium salt comprising Sodium chloride;
    a selenium salt comprising Sodium selenite;
    a silicon comprising Sodium silicate;
    a sulfite salt comprising Sodium sulfite;
    a tellurium salt comprising Sodium tellurite;
    a strontium salt comprising Strontium sulfate; and sulfur.

14. A dentifrice for a tooth and an oral cavity comprising:
    de-ionized water;
    a thickener;
    a humectant;
    an abrasive;
    a foaming agent;
    a water soluble calcium salt;
    a water soluble phosphate salt;
    about 0.1 to about 0.4 weight percent ubiquinone;
    a carbonate salt selected from a group consisting of Ferrous carbonate, Magnesium carbonate, and Sodium carbonate;
    a sulfide salt;
    a lithium salt;
    a magnesium salt selected from a group consisting of Magnesium bromide and Magnesium chloride;
    an iodide salt;
    a sulfate salt selected from a group consisting of Magnesium sulfate, Potassium sulfate, and Sodium sulfate;
    a potassium salt;
    rubidium;
    a boron salt;
    a sodium salt;
    a selenium salt;
    a silicon;
    a sulfite salt;
    a tellurium salt;
    a strontium salt; and sulfur.

* * * * *